United States Patent [19]
Chevallet et al.

[11] 3,953,897
[45] May 4, 1976

[54] VESICAL PROSTHESIS

[75] Inventors: Jacques Chevallet, Nogent-sur-Marne; André Sausse, Sceaux, both of France

[73] Assignee: Rhone-Poulenc, S.A., Paris, France

[22] Filed: Dec. 27, 1974

[21] Appl. No.: 536,795

[30] Foreign Application Priority Data
Dec. 28, 1973 France............................ 73.46764

[52] U.S. Cl................................. 3/1; 128/DIG. 21
[51] Int. Cl.² ............................................ A61F 1/24
[58] Field of Search........... 3/1; 128/334 R, DIG. 21, 128/DIG. 25, 349, 294, 295

[56] References Cited
UNITED STATES PATENTS

| | | | |
|---|---|---|---|
| 2,379,346 | 6/1945 | Farrell | 128/295 |
| 3,604,424 | 9/1971 | Windom | 128/295 |
| 3,783,454 | 1/1974 | Sausse et al. | 3/1 |
| 3,862,452 | 1/1975 | Wichterle et al. | 3/1 |

FOREIGN PATENTS OR APPLICATIONS

| | | | |
|---|---|---|---|
| 181,242 | 10/1966 | U.S.S.R. | 3/1 |
| 2,116,838 | 7/1972 | France | 3/1 |
| 1,156,935 | 11/1963 | Germany | 3/1.4 |

OTHER PUBLICATIONS

"A Prostuetic Heart With Hemispherical Ventricles Designed for Low Hemolytic Action" by Clifford Kwan–Gett et al., *Transactions Amer. Soc. Artificial Internal Organs*, Vol. XVI, 1970 pp. 409–415.

"Bladder Regeneration After Cystectomy and Prostuetic Urinary Bladder Replacement" by T. H. Stanley et al., *Transaction A.S.A.I.O.*, Vol. XVII, 1971, pp. 134–137.

*Primary Examiner*—Ronald L. Frinks
*Attorney, Agent, or Firm*—Stevens, Davis, Miller & Mosher

[57] ABSTRACT

An implantable vesical prosthesis for a bladder which includes a sterile pouch formed from flexible plastics material compatible with the organs surrounding the natural bladder of a patient, at least a portion of the pouch being deformable during the introduction and discharge of urine between two extreme positions, one corresponding to the full pouch and one to the empty pouch. Two inlet pipes open into the interior of the pouch and are connectable to two ureters of a patient and an outlet pipe is connectable to the urethra. The prosthesis is completely void of any internal artificial valves or flaps.

11 Claims, 3 Drawing Figures

VESICAL PROSTHESIS

The present invention relates to an implantable vesical prosthesis intended to replace the failing bladder of a patient.

Some affections, and especially cancerous affections, make it necessary to remove the bladder completely. It has already been proposed in the patent published under French Pat. No. 2,116,838 to place an artificial bladder in position, the said bladder being connected to the two ureters and to the urethra of a patient and being equipped with systems of three internal valves, one of which operates in the opposite direction to the other two, a device which controls the valve by means of an auxiliary fluid contained in an attached pouch and a safety device. Such a combination is rather complex and cannot always be relied upon.

According to the present invention we provide an implantable vesical prosthesis for a bladder, comprising a sterile pouch formed of flexible plastics material compatible with the organisms surrounding a natural bladder, at least a portion of the pouch being deformable during the introduction and discharge of urine, between two extreme positions, one corresponding to the full pouch and one to the empty pouch, two inlet pipes opening into the interior of said pouch at inlet orifices and connectable to the two ureters of a patient, an outlet pipe connectable to a urethra of a patient, the prosthesis being devoid of any internal artificial valve or flap.

Such a construction can carry out the main functions of a natural bladder, is simple and economical to manufacture, easy to place in position and the functioning of it can be controlled naturally.

Preferably, one of these two extreme positions corresponds to a stable form and the other to a metastable form of the prosthesis.

In order that the invention may more readily be understood, the following description is given, merely by way of example, reference being made to the accompanying drawings, in which.

The prosthesis comprises a vesical pouch made of flexible plastic which is compatible with the organism and which can be sterilised, and is, for example, made of silicone elastomer. The shape can vary and can be, for example, cylindrical, toroidal and the like, and is decided in accordance with the implantation envisaged in order to prevent it from becoming folded over on itself. When in the full position, this vesical prosthesis can have a volume of the order of 300 to 500 cm³ in the case of an adult man. It is intended to replace the natural bladder of a patient after the bladder has been removed and after the prosthesis has been connected to the ureters and to the urethra. It can occupy any intra-abdominal cavity whatsoever, but preferably occupies the site of the natural bladder; after the operation, it generally remains completely invisible. The vesical pouch generally possesses three pipelines at the side, two of which can be connected to the ureters of the patient and the third to the urethra, in accordance with known surgical techniques, if necessary introducing the prosthesis into the urethra in order to retain the course of the flow through the natural routes.

It has been found that when a vesical prosthesis is connected to the ureters and to the urethra of a patient, the peristaltic effect of the ureters prevents the urine from flowing backwards and the sphincter of the urethra gives the desired sealing effect. The prosthesis according to the invention is thus a complete vesical prosthesis which is devoid of any valve or any artificial flap. The manufacture of such a prosthesis is particularly simple and economical, it is easy to place it in position and its functioning is much safer since it is controlled by the patient himself.

Figure 1:
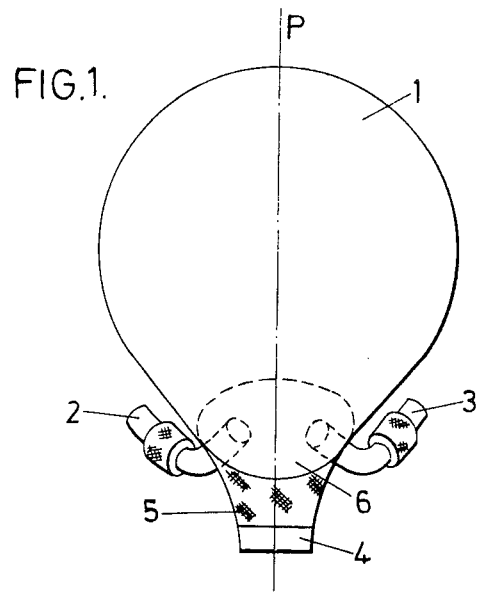
FIG. 1 is a view in elevation of a first embodiment of the prosthesis according to the invention.
Figure 2:
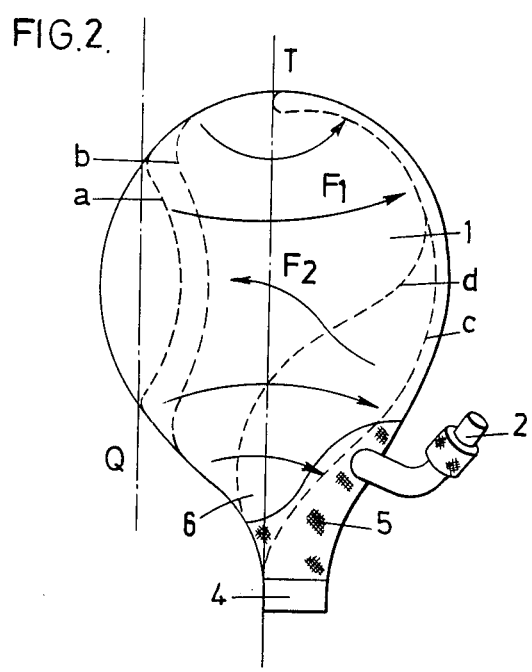
FIG. 2 is a view from the left of the prosthesis of FIG. 1.

The prosthesis represented in FIGS. 1 and 2 is a preferred embodiment. Seen in elevation (FIG. 1), the prosthesis has a plane of symmetry P. When it is full, the vesical pouch 1 has substantially the shape of an ellipsoid or of a sphere possessing an elongated bulge 6 at the lower part, the bulge not undergoing deformation readily. The combination can have the general shape of a pear pointing downwards.

Advantageously, orifices equipped with pipelines connecting the vesical pouch to the ureters and to the urethra are grouped on the lower bulge 6. Pipes 2 and 3 are generally symmetrical relative to the plane P and the pipe 4, which is wider by comparison, is advantageously situated at the lower part of the prosthesis and opens downwards. If necessary, the pipelines 2 and 3 can be connected to one or two artificial ureters of the type described especially in the patent published under French Pat. No. 2,133,083. The pipe 4 can be connected to the urethra. In the upper part of the prosthesis, the wall is generally very thin (its thickness is of the order of a millimeter) and it is made of a flexible material which undergoes deformation readily and which is practically devoid of elasticity.

Since the prosthesis according to the preferred embodiment of the invention generally does not contain any air, its volume gradually tends to become less as the liquid initially present flows out. A portion of the side wall which bulges outwards changes concavity over a zone corresponding substantially to a spherical or ellipsoidal dome and assumes the profile (a), which is locally concave and symmetrical, about a plane Q, to the previous convex profile. As the internal volume of the prosthesis continues to diminish, the concave profile (a) undergoes deformation, gradually at first, in the direction of the arrows $F_1$ and becomes identical successively with the profile (b), and then rapidly with the profile (c), and this expels the remaining liquid. The internal capacity of the prosthesis has then become practically negligible. It can be seen in FIG. 2 that the wall of the prosthesis undergoes deformation in a substantially symmetrical manner relative to a plane T, which is approximately a diametral plane of the prosthesis and is tangential internally to the pipeline 4.

The prosthesis then possesses convex and concave walls fitted into one another, which give it externally the shape of a dome.

When the prosthesis fills up again with liquid, the latter exerts an increasing pressure on the wall with the profile (c) and deforms it in accordance with the arrow $F_2$ to give it successively the profiles (d), (b) and (a), and then this wall becomes convex again, as represented in FIG. 2.

These prostheses are generally made from elastomers, for example silicone elastomers. Depending on whether the elastomer is vulcanized when the prosthesis is in the full or empty position, it thereafter assumes stable behaviour in the full position and metastable behaviour in the empty position, or vice versa.

These prostheses are considered to have a stable shape when, after having been substantially deformed, their walls always return spontaneously to their original position, in the absence of external forces. On the other hand, they have a metastable shape when, after having been deformed, their walls return spontaneously only for a limited period of time to a position similar to their original position, in the absence of external forces. Only very small external forces are required in order to make a prosthesis function when close to these two extreme positions, the main force being provided by the internal tensions of the walls which are released rapidly and work together to give the walls a stable or metastable bulging shape, when the prosthesis becomes either full or empty.

It has been observed that, due to this particular characteristic, the process of emptying the prosthesis completely was both facilitated and accelerated and that, moreover, its complete filling was easier.

It has also been observed that, under these conditions, the muscles of the patient, and especially the abdominal muscles, have to exert only a limited pressure on the prosthesis in order to empty it completely and rapidly.

Figure 3:
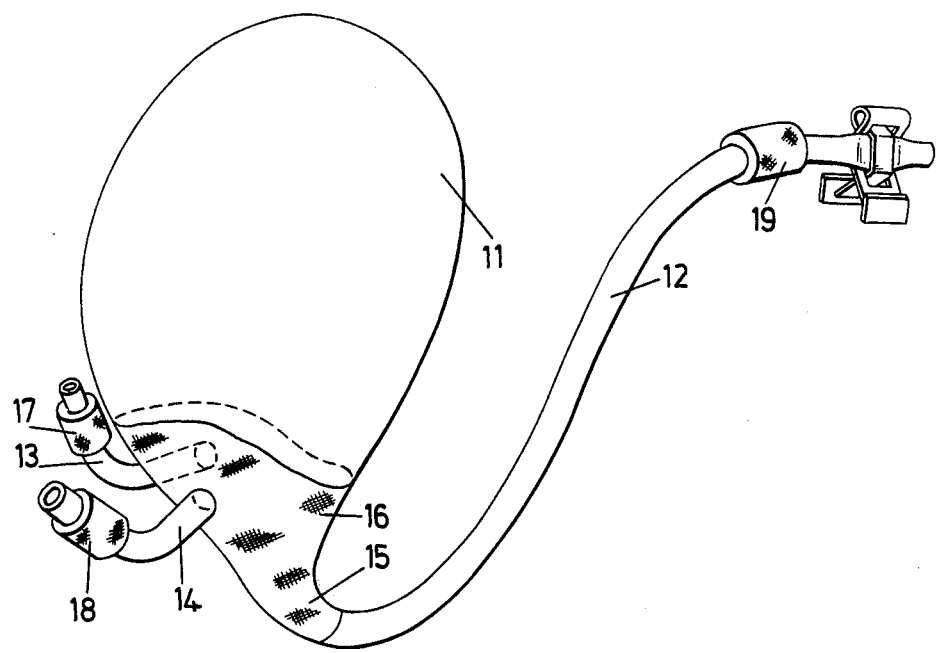
FIG. 3 is a view in elevation of a second embodiment.

The pipes intended for the ureteral connections and/or for discharging urine through the abdominal or perineal wall can be an integral part of the vesical prosthesis. These pipelines together with the vesical pouch are then made in a single unit. FIG. 3 thus represents a prosthesis which is both a vesical and a urethral prosthesis. The pipe 12, connected to the base 15 of the vesical pouch 11, passes through the abdominal or perineal wall of the patient at the position chosen by the surgeon. A sleeve of polyester velour 19 makes it possible to suture it to the cutaneous tissues. The prosthesis remains invisible after the operation, except for the distal end of the pipe 12. At its side, in the reinforced zone 16, the vesical pouch possesses two other pipes 13 and 14 intended to be connected to the ureters of the patient or to artificial ureters. The pipe 12 is generally made from the same materials as the vesical pouch 11, because it is also very flexible; its length is usually between 2 and 40 cm. Near its distal end, the pipe 12 is equipped with a sealing means of known type (not shown) which can be manipulated easily by the patient himself. The pipe can, for example, be closed by means of a clip, a plug or a stop-clock.

Likewise, a single prosthesis can also replace a bladder together with one or two ureters. The pipes replacing the ureters advantageously possess a thin wall forming helical undulations in order to retain great flexibility whilst avoiding the danger that the pipes might become blocked undesirably.

Although the prosthesis according to the invention is preferably made of silicone elastomer, it can also be made of any flexible material such as a natural or synthetic rubber or a thermoplastic resin like polyethylene. The prosthesis according to the invention can also be made of bioresorbable materials such as collagen, polylactides, polysuccinates, polyoxalates and the like.

The process for manufacturing a vesical prosthesis made of silicone elastomer is similar, in its essential aspects, to the process for manufacturing prostheses to provide cardiac assistance or cardiac prostheses described, for example, respectively in French Pat. Nos. 1,499,305 and 1,538,644. It is also possible to use a blow-moulding technique.

In every case, the prosthesis is covered over its entire inner surface, and advantageously at least partially over its outer surface, with a smooth coating of vulcanized silicone elastomer. This coating forms a lacquering of the walls of the prosthesis, and on the one hand, this prevents concretions or various residues from being deposited and caught on the inner walls and, on the other hand, facilitates the relative movements and the toleration of the prosthesis amongst the natural organs between which it is inserted. This lacquering can be carried out especially in accordance with the technique described in the patent published under French Pat. No. 2,126,573.

The walls of the prosthesis according to the invention can advantageously be reinforced, at least locally, by a textile element firmly fixed to the wall, for example embedded inside the latter. This textile element absorbs a large part of the mechanical stresses to which the prosthesis is subjected. It is generally placed in the zones which are subjected to considerable stresses, for example, in the zone on which the three pipes connected to the ureters and to the urethra are positioned. It is also possible to embed a textile element in the outer wall of the dome which undergoes practically no deformation and which can, without disadvantage, be a little less flexible than the opposite wall. As the textile element, it is possible to use, for example, a gauze woven from polyester yarns which allows the prosthesis to retain sufficient flexibility.

In order to facilitate the suturing of the ureters and the urethra to the pipes, 2, 3 and 4 respectively, it is advantageous to surround the pipes with a sleeve made of a suturable and colonizable textile material. Moreover, in order partially to fix th prosthesis to the surrounding tissues, it is also advantageous to cover with colonizable material the zone of the prosthesis to which the pipelines are attached. Textile materials chosen from amongst the following: short-nap velour, especially made of polyesters or polyamides and woven fabrics, especially made of polyesters, can be used as the colonizable and suturable material. It is also possible to use an open-cell foam, especially made of polyurethane, as the colonizable material. It is preferred to use a velour, and especially a polyester velour, for example in accordance with the technique already described in ASAIO, volume XV, 1969 — pages 25–27 and volume XVII 1971 — pages 134–137.

The prosthesis according to the invention can be placed in position in accordance with known surgical techniques. It can be placed in position in man or in animals. It can be the subject of various different embodiments which lie within the ability of those skilled in the art, without going outside the scope of the present invention. For example, it can possess only two orifices, one connected to the urethra and the other to the ureters via a Y-shaped nozzle.

Prostheses according to the invention have been tested experimentally in dogs and they function and behave altogether satisfactorily for one month after they have been placed in position.

We claim:

1. An implantable vesical prosthesis for a bladder, comprising a sterile pouch formed of flexible plastics material compatible with the organisms surrounding a natural bladder, at least a portion of the pouch being deformable during the introduction and discharge of urine, between two extreme positions one corresponding to the full pouch and one to the empty pouch, two inlet pipes opening into the interior of said pouch at inlet orifices and connectable to the two ureters of a patient, an outlet pipe connectable to a urethra of a patient the prosthesis being devoid of any internal artificial valve or flap.

2. A vesical prosthesis as claimed in claim 1, wherein said deformable portion of the wall of said pouch bulges outwards, is convex towards the outside and is metastable when the pouch is empty.

3. A vesical prosthesis as claimed in claim 1, wherein said deformable portion of the wall of said pouch bulges outwards, is convex towards the outside and metastable when the pouch is full, and is concave towards the outside and stable when the pouch is empty.

4. A vesical prosthesis as claimed in claim 2, wherein the deformable bulging portion of the wall can change concavity over a zone corresponding substantially to a spherical or ellipsoidal dome.

5. A vesical prosthesis as claimed in claim 3, wherein the deformable bulging portion of the wall can change concavity over a zone corresponding substantially to a spherical or ellipsoidal dome.

6. A vesical prosthesis as claimed in claim 1, and further comprising, a substantially non-deformable region of said pouch, said orifices being grouped in said region.

7. A vesical prosthesis as claimed in claim 1, wherein the outlet pipe and the vesical pouch are made as a single unit.

8. A vesical prosthesis as claimed in claim 1, wherein the outlet pipe further comprises external sealing means which can be manipulated by the patient.

9. A vesical prosthesis as claimed in claim 1, wherein the pipes which can be connected to the ureters have thin fluid-tight walls forming helical undulations.

10. A vesical prosthesis as claimed in claim 1, wherein the prosthesis is made at least partially by a bioresorable material.

11. A vesical prosthesis as claimed in claim 1, wherein the inlet pipes and the vesical pouch are made as a single unit.

* * * * *